United States Patent [19]

Timmer et al.

[11] Patent Number: 4,831,008
[45] Date of Patent: May 16, 1989

[54] METHOD FOR THE PREPARATION AND APPLICATION OF RHODIUM CATALYSTS FOR THE HYDROGENATION OF AROMATIC AND OTHER UNSATURATED COMPOUNDS UNDER MILD CONDITION

[75] Inventors: Klaas Timmer, Bilthoven; Harmen A. Meinena, Leusden; Eric J. Bulten, Blaricum, all of Netherlands

[73] Assignee: Nederlandse Organisatie voor Toegepast Natuurwetenschappelijk Onderzoek tno, The Hague, Netherlands

[21] Appl. No.: 171,665

[22] Filed: Mar. 22, 1988

[30] Foreign Application Priority Data

Mar. 24, 1987 [NL] Netherlands ................ 8700691

[51] Int. Cl.$^4$ .................... B01J 23/46; B01J 23/58
[52] U.S. Cl. .................................. 502/328; 502/325
[58] Field of Search .............................. 502/325, 328

[56] References Cited

U.S. PATENT DOCUMENTS

| 4,174,298 | 11/1979 | Antos | 502/325 X |
| 4,175,056 | 11/1979 | Antos | 252/441 |
| 4,243,824 | 1/1981 | Noltes | 585/259 |
| 4,271,302 | 6/1981 | McVicker | 546/2 |

FOREIGN PATENT DOCUMENTS

| 0037716 | 10/1981 | European Pat. Off. |
| 2810198 | 9/1978 | Fed. Rep. of Germany |
| 8023595 | 5/1982 | France |

OTHER PUBLICATIONS

J. of Catalysts, vol. 98, No. 2, Apr. 1986, pp. 554–558, Academic Press Inc.; G. M. Nunez et al: "Rh/SiO$_2$ and Rh/Al$_2$O$_3$ Catalysts."
Effect of Precursor and H$_2$ Pretreatment on Chemisorption and Catalytic Activity.
Chemical Abstracts, 89(2), 11/13/78, p. 407, abstract #169703e, M. Ichikawa: "Catalysis by Supported Metal Crystallites from Carbonyl Cluster. II. Catalytic Ethanol Synthesis from Carbon Monoxide and Hydrogen under Atmospheric Pressure over Supported Rhodium Crystallites Prepared Rh from Carbonyl Clusters Deposited on Titanium Dioxide, Zirconium Oxide, and Lanthanun Oxide."

*Primary Examiner*—W. J. Shine
*Attorney, Agent, or Firm*—Rosen, Dainow & Jacobs

[57] ABSTRACT

Method for the preparation of catalysts on support materials, such as strontiumtitanate, which serve for the hydrogenation of unsaturated organic compounds such as alkenes, alkynes and aromates, which catalysts consist of rhodium-metal on support, obtained by applying rhodiumcarbonyl-clusters to a support in an inert atmosphere and then pyrolyzing them at a relatively low temperature of for instance 150° C.

The material, thus applied to the support is activated by means of a reaction with oxygen, preferably between 0° and 150° C.

6 Claims, No Drawings

METHOD FOR THE PREPARATION AND APPLICATION OF RHODIUM CATALYSTS FOR THE HYDROGENATION OF AROMATIC AND OTHER UNSATURATED COMPOUNDS UNDER MILD CONDITION

The invention concerns a method for the preparation of new rhodium catalysts (metal on support) with a relatively low rhodium content, starting from rhodium carbonyl clusters which are precipitated on a support in an inert atmosphere ($N_2$), and then are pyrolyzed at a relatively low temperature (Tmax. 300° C.), and are finally activated by means of reaction with oxygen (oxygen gas or oxygen in the air can act as an oxygen source), and also a method for the hydrogenation of aromatic and other unsaturated compounds with the aid of these catalysts, both in the liquid phase and in the gas phase, under mild conditions, such as, for example, 1 atmosphere $H_2$ and room temperature up to a maximum of 70° C.

Rhodium catalysts, their preparation and their application in the hydrogenation particularly of aromatic hydrocarbons under mild conditions, are known and are described, for example, in:

R. Egli and C.H. Eugster, Helv. Chim. Acta, 58, 2321 (1975).

R. Lamartine, R. Perrin and G. Bertholon, C.R. Acad. Sc. Paris, 291, 219 (1980).

G. Vitulli, P. Salvadori, A. Raffaelli, P. A. Constantino and R. Lazzaroni, J. Organometal. Chem., 239, C23 (1982).

J. G. Noltes, G. v. Koten and M. S. Cohen, U.S. Pat. No. 4,243,824 (1981).

As is described in detail below it has now been discovered that very active rhodium catalysts with a relatively low weight percentage of rhodium can be prepared on a support which are capable of promoting the hydrogenation of particularly aromatic hydrocarbons under mild conditions and with a relatively high activity in relation to existing catalysts. These catalysts are prepared by applying rhodium carbonyl clusters in an inert atmosphere on a suitable support, then by pyrolyzing these clusters at a relatively low temperature, and then by activating the material which has been obtained in this manner by means of reaction with oxygen according to the invention. The pyrolyzing process takes place at temperatures between 100° C. and 300° C., and preferably at temperatures around 150° C. The activation of the catalyst by means of reaction with oxygen takes place at temperatures between 0° C. and 150° C.

Similar catalysts are known and are used, for example, in synthesis gas chemistry ($CO + H_2$ reactions), aimed at promoting the selective synthesis of, for example, MeOH, EtOH or $CH_4$, and are described inter alia in:

M. Ichikawa, Bull. Chem. Soc. Jpn., 51, 2268 and 2273 (1978).

M. Ichikawa, J.C.S. Chem. Comm., 1978, 566.

A. Ceriotti, S. Martinengo, L. Zanderighi, C. Tonelli, A. Iannibello and A. Girelli, J. Chem. Soc. Farad. Trans I. 80, 1605 (1984).

Such known catalysts are, however, prepared under stringent exclusion of oxygen, and in this form they do not appear to be suitable as catalysts for the hydrogenation of aromatic and other unsaturated compounds.

The surprising thing about the present invention is that after reaction with oxygen hydrogenation catalysts are obtained with an unexpectedly high activity.

Examples of known rhodium carbonyl clusters which are used according to the invention are $Rh_4(CO)_{12}$ and $Rh_6(CO)_{16}$; $Rh_4(CO)_{12}$ is prefer These clusters are commercially obtainable (Strem Chemicals, Drijfhout & Zoon's). Examples of supports which are used according to the invention are $TiO_2$-anatase, $TiO_2$-rutile, $SrTiO_3$, $BaTiO_3$, $SrZrO_3$, $Al_2O_3$ and $SiO_2$; $TiO_2$ (anatase and rutile), $BaTiO_3$ and $SrTiO_3$ are preferred and $SrTiO_3$ is most preferably used. These supports are all commercially available (Bayer, Ventron, Degussa).

Examples of compounds which can be hydrogenated with the aid of the catalysts according to the invention at approx. 1 atmosphere $H_2$ and at room temperature up to approx. ±70° C. are aromatic compounds, alkenes, alkynes, nitriles, ketones and nitro compounds.

A form of implementation of a method for the preparation of the catalysts according to the invention is that a rhodium carbonyl cluster is dissolved in an inert solvent (hexane, chloroform, dichloromethane, toluene) in an inert atmosphere ($N_2$); then such a quantity of a pre-dried support (2 hours at 200° C., pressure $\leq 1$ mm Hg) is added to this solution that the final catalyst will contain 0.5 to 2.5 weight percent of rhodium. The suspension which is obtained is slowly evaporated until dry at a low temperature and under reduced pressure. The remaining powder is subjected to a vacuum (pressure $\leq 1$ mm Hg) and the temperature is brought to 150° C.; these conditions are then maintained for 2 hours. After cooling-off to room temperature the grey-coloured powders which are obtained in this manner are then brought into contact with air; they are stored in contact with the air.

A method for testing the catalysts according to the invention as to their activity in the hydrogenation of substrates in the liquid phase at approx. 1 atmosphere $H_2$ and a certain temperature is that a quantity of catalyst is added to a quantity of substrate, or that a quantity of catalyst is added to a solution of the substrate in a solvent (MeOH, EtOH, $H_2O$, cyclohexane); then at a certain temperature the air present above is replaced by $H_2$, after which the reaction vessel is connected up to a storage vessel filled with $H_2$ at approx. 1 atmosphere pressure. The reaction is started by means of stirring or shaking and the reaction speed is determined by measuring the quantity of the $H_2$-take-up.

A method for testing the catalysts according to the invention as to their activity in the hydrogenation of substrates in the gas phase at room temperature is that a gas mixture containing hydrogen and substrate is passed over a quantity of catalyst and then through a cold drop (−80° C.), in which the products condense.

Experimental research shows that the affinity for hydrogen of the catalysts according to the invention is extremely high: the $H_2$-adsorption to the catalysts found is 4 times [G. M. Nunez, A. R. Patrignani and A. J. Rouco, J. Catal., 98 554 (1986)] to 8 times [H. Fujitsu, N. Ikeyama and I. Mochida, J. Catal., 100, 279 (1986)] as high (see table A) as is mentioned in the literature for classical catalysts whereby rhodium is applied to a support via $RhCl_3$. The $H_2$-adsorption to hydrogenation catalysts (metal on support) is considered to be a measurement for the distribution of the metal on the support and for the activity which can be expected as a catalyst in hydrogenation. The $H_2$-adsorption to the catalysts according to the invention is fast and largely occurs within 5 minutes.

The high activity of the catalysts according to the invention in the hydrogenation of various substrates, particularly aromatic substrates in the liquid phase at approx. 1 atmosphere $H_2$ and at room temperature up to a maximum of 70° C. results in high turnover numbers, which indicate the number of H-atoms which are transferred to the substrate per rhodium atom per unit of time. These turnover numbers given in tables B to G are high in comparison with corresponding figures given in the literature (see refs. on page 1).

In the gas phase the hydrogenation of benzene at room temperature in the presence of a catalyst according to the invention takes place exothermally, while the presence of methane is not disturbing (table H).

The activating energy for the hydrogenation of toluene in the presence of 0.5 weight percent Rh on $TiO_2$-anatase (Degussa P25), prepared according to example 1, turns out to amount to 5 to 6 Kcal/Mol. This is lower than is mentioned in the literature for the hydrogenation of toluene in the presence of a number of group VIII metal catalysts, where activating energies are mentioned from 7.4 Kcal/Mol [J. Volter et al., J. Catal., 12, 307 (1968)] to 17.5 Kcal/Mol [G. Lietz et al., Mechanisms of hydrocarbon reactions, 1973, 151].

The catalysts according to the invention show stereo selectivity; in the hydrogenation of o-xylene mainly cis-1,2-dimethylcyclohexane is formed (see table B).

IMPLEMENTATION EXAMPLES

EXAMPLE 1

Preparation of 0.5 weight percent Rh on $SrTiO_3$.

In an inert atmosphere ($N_2$) $Rh_4(CO)_{12}$ (0.23 g=0.31 mMol) was dissolved in 100 ml of hexane. 25 g of pre-dried $SrTiO_3$ (2 hours, 200° C., 1 mm Hg) was added to the red solution. The resulting suspension was then slowly evaporated at a low temperature ($\leq 25°$ C.) and under reduced pressure. The remaining beige to very light red powder was subjected to a vacuum ($\leq 1$ mm Hg) and the temperature was brought to 150° C. (in circa 0.75 hours); these conditions were then maintained for 2 hours. After cooling to room temperature the now grey-brown powder was brought into contact with oxygen in the air, homogenized, bottled and stored in contact with the air.

Yield : $\approx 25$ g 0.5 weight % Rh on $SrTiO_3$.
Colour : light grey-brown.

EXAMPLE 2

Preparation of 1.0 weight percent Rh on $SrTiO_3$.

Method as described in example 1, but now the $Rh_4(CO)_{12}$ was dissolved in a mixture of 10 ml of dichloromethane and 5 ml of pentane, while only 12.5 g $SrTiO_3$ was added.

Yield : $\approx 12.5$ g 1.0 weight % Rh on $SrTiO_3$.
Colour : grey-brown.

EXAMPLE 3

Preparation of 2.5 weight percent Rh on $SrTiO_3$

Method as described in example 1, but the $Rh_4(CO)_{12}$ was now dissolved in 10 ml of dichloromethane, while only 5 g $SrTiO_3$ was added.

Yield : $\approx 5$ g 2.5 weight % Rh on $SrTiO_3$.
Colour : dark-grey.

EXAMPLE 4

Preparation of 0.5 weight percent Rh on $SrTiO_3$

In an inert atmosphere ($N_2$) $Rh_6(CO)_{16}$ (0.22 g=0.21 mMol) was put into 500 ml of dichloromethane. The resulting suspension was stirred for 16 hours, after which most of the $Rh_6(CO)_{16}$ was dissolved. 25 g predried $SrTiO_3$ (2 hours 200° C., 1 mm Hg) was added to the brown solution. The resulting suspension was evaporated slowly at a low temperature ($\leq 25°$ C.) and under reduced pressure. The remaining powder was subjected to a vacuum ($\leq b$ 1 mm Hg) and the temperature was brought to 150° C. (in circa 0.75 hours); these conditions were then maintained for 2 hours. After cooling to room temperature the powder was brought into contact with oxygen in the air, homogenized, bottled, and stored in contact with the air.

Yield : $\approx 25$ g 0.5 weight % Rh on $SrTiO_3$.
Colour : light grey-brown.

EXAMPLE 5

Determination of $H_2$-adsorption to catalysts of the type Rh on a support

At room temperature (20° C.) 2 g of catalyst (0.5 weight % Rh on support; Rh from $Rh_4(CO)_{12}$) or 2 g of support were suspended in 15 ml of solvent. The air above was replaced by $H_2$, the reaction vessel was connected up to a gas burette filled with $H_2$ at approx. 1 atmosphere pressure. With the aid of a shaking machine shaking was carried out for 15 minutes and the $H_2$-adsorption to the catalysts was determined via the measurement of the $H_2$-take-up. The results are given in table A.

TABLE A

| | | | | |
|---|---|---|---|---|
| $H_2$-adsorption to supports and Rh-catalysts (0.5 weight % Rh[f] on support) at approx. 1 atmosphere $H_2$ and 20° C. | | | | |
| support | Rh [mAt] | solvent | $H_2$ taken up [mMol] | Adsorption $H_2$ [mAt H/mAt Rh] |
| $SrTiO_3$[a] | — | cyclohexane | 0 | — |
| $SrTiO_3$ | $9.72 \times 10^{-2}$ | toluene | $0^e$ | — |
| $SrTiO_3$ | $9.72 \times 10^{-2}$ | cyclohexane | $20.8 \times 10^{-2}$ | 4.28 |
| $TiO_2$-anatase[b] | — | cyclohexane | 0 | — |
| $TiO_2$-anatase | $9.72 \times 10^{-2}$ | toluene | $0^e$ | — |
| $TiO_2$-anatase | $9.72 \times 10^{-2}$ | cyclohexane | $20.8 \times 10^{-2}$ | 4.28 |
| $TiO_2$-anatase[c] | — | cyclohexane | 0 | — |
| $TiO_2$-anatase | $9.72 \times 10^{-2}$ | cyclohexane | $16.7 \times 10^{-2}$ | 3.44 |
| $TiO_2$-anatase | — | ethanol | 0 | — |
| $TiO_2$-anatase | $9.72 \times 10^{-2}$ | ethanol | $16.7 \times 10^{-2}$ | 3.44 |
| $TiO_2$-rutile[d] | — | cyclohexane | 0 | — |
| $TiO_2$-rutile | $9.72 \times 10^{-2}$ | cyclohexane | $12.5 \times 10^{-2}$ | 2.58 |
| — | — | cyclohexane | 0 | — |

TABLE A-continued

H$_2$-adsorption to supports and Rh-catalysts (0.5 weight % Rh$^f$ on support) at approx. 1 atmosphere H$_2$ and 20° C.

| support | Rh [mAt] | solvent | H$_2$ taken up [mMol] | Adsorption H$_2$ [mAt H/mAt Rh] |
|---|---|---|---|---|
| — | — | ethanol | 0 | — |

$^a$Ventron
$^b$Degussa P25
$^c$Bayer Titan A
$^d$Ventron
$^e$"Catalyst" before activating with oxygen
$^f$Rh from Rh$_4$(CO)$_{12}$.

EXAMPLE 6

Hydrogenations of pure substrate in the liquid phase.

12.5 ml of substrate and 0.5 g of catalyst were placed in a double-walled hydrogenation vessel; with the aid of a thermostat bath the desired temperature was adjusted, the air above was replaced by H$_2$ and the vessel was connected up to a gas burette filled with H$_2$ at approx. 1 atmosphere pressure. By means of a shaking machine the reaction was started and maintained; via measuring the H$_2$ take-up the reaction speed (turnover numbers) was determined during 1 or more hours.

The tables B and C show the results, which were obtained with the above method.

TABLE B

Hydrogenation of aromates with the aid of Rh-catalysts (0.5 weight % Rh on support)

| Compound | Source Rh | Support | Temp °C. | TN 1st hr.$^e$ | TN after 4 hours$^e$ |
|---|---|---|---|---|---|
| Benzene | Rh$_4$(CO)$_{12}$ | SrTiO$_3$$^a$ | 30 | 2748 | 2372 |
| Toluene | Rh$_4$(CO)$_{12}$ | SrTiO$_3$ | 50 | 28$^h$ | — |
| Toluene | Rh$_4$(CO)$_{12}$ | SrTiO$_3$ | 30 | 1541 | 1100 |
| Toluene | Rh$_4$(CO)$_{12}$ | TiO$_2$-anatase$^b$ | 30 | 1450 | 919 |
| Toluene | Rh$_4$(CO)$_{12}$ | BaTiO$_3$$^a$ | 19 | 1087 | — |
| Toluene | Rh$_4$(CO)$_{12}$ | TiO$_2$-rutile$^a$ | 30 | 1075 | 904 |
| Toluene | Rh$_4$(CO)$_{12}$ | SrZrO$_3$$^c$ | 19 | 879 | — |
| Toluene | Rh$_4$(CO)$_{12}$ | SiO$_2$$^a$ | 20 | 514 | — |
| Toluene | Rh$_4$(CO)$_{12}$ | TiO$_2$-anatase$^d$ | 50 | 0$^h$ | — |
| Toluene | Rh$_4$(CO)$_{12}$ | TiO$_2$-anatase$^d$ | 30 | 869 | 752 |
| Toluene | Rh$_6$(CO)$_{16}$ | SrTiO$_3$ | 30 | 858 | 703 |
| Toluene | Rh$_6$(CO)$_{16}$ | TiO$_2$-rutile | 30 | 417 | 350 |
| Toluene | Rh$_6$(CO)$_{16}$ | TiO$_2$-anatase$^b$ | 30 | 487 | 378 |
| o-Xylene | Rh$_4$(CO)$_{12}$ | SrTiO$_3$ | 30 | 195 | — |
| o-Xylene | Rh$_4$(CO)$_{12}$ | TiO$_2$-anatase$^d$ | 30 | 173 | — |
| o-Xylene | Rh$_4$(CO)$_{12}$ | TiO$_2$-anatase$^d$ | 50 | $f,g$ | — |

$^a$Ventron
$^b$Bayer-Titan A
$^c$Alfa
$^d$Degussa P25
$^e$TN = Turnover Number = mAt H/mAt Rh/hour
$^f$GLC: cis- & trans-1,2-dimethylcyclohexane; cis/trans = 82.5/12.5
$^g$TN after 19 hours is 135
$^h$"Catalyst" before activating with oxygen

TABLE C

Hydrogenation of toluene with the aid of an Rh-catalyst (0.5 weight % Rh$^b$ on TiO$_2$-anatase$^c$)

| Temp °C. | TN 1st hour$^a$ |
|---|---|
| 12 | 342 |
| 20 | 524 |
| 30 | 628 |
| 40 | 882 |
| 50 | 1022 |
| 60 | 1216 |
| 70 | 1084 |

$^a$TN = Turnover Number = mAt H/mAt Rh/hour
$^b$Rh from Rh$_4$(CO)$_{12}$.
$^c$Degussa P25

EXAMPLE 7

Hydrogenations of pure substrate in the liquid phase. Method as described in example 6, but now with 25 or 50 ml of substrate and 0.2 to 3.0 g of catalyst, while now the reaction is started and maintained by means of stirring. Table D shows the results which were obtained with the above method.

TABLE D

Hydrogenations according to the method of example 7 with the aid of Rh$^a$-catalysts

| Compound | Support | Weight Rh (%) | Quantity Catalyst/Substrate (g/ml) | Temp. (°C.) | T.N. 1st hour$^d$ | T.N. (after x hours)$^d$ |
|---|---|---|---|---|---|---|
| toluene | SrTiO$_3$$^b$ | 0.5 | 1.0/50 | 50 | 935 | — |
| toluene | SrTiO$_3$ | 1.0 | 0.5/50 | 50 | 1233 | — |
| toluene | SrTiO$_3$ | 2.5 | 0.2/50 | 50 | 1140 | — |
| acetone | TiO$_2$-anatase$^c$ | 0.5 | 1.0/25 | 25 | 0 | — |
| ethyl-benzoate | TiO$_2$-anatase | 0.5 | 1.0/25 | 69 | 86 | 80(2) |
| diethyl-terephtalate | TiO$_2$-anatase | 0.5 | 1.0/25 | 69 | 36 | 50(5) |
| diethyl-terephtalate | TiO$_2$-anatase | 0.5 | 3.0/25 | 62 | 87 | 66(10)$^e$ |

$^a$Rh from Rh$_4$(CO)$_{12}$
$^b$Ventron
$^c$Bayer Titan A
$^d$T.N. = Turnover Number = mAt H/mAt Rh/hour
$^e$H—NMR: product is 1,4-diethyl cyclohexane dicarboxylate; no ester reduction

EXAMPLE 8

Hydrogenations of substrate in a solvent.
16 to 25 ml of a solvent (methanol, ethanol, water, cyclohexane), 10 to 100 mMol of substrate and 0.5 to 1.0 g of catalyst were placed in a reaction vessel. The air above was replaced by $H_2$ and the vessel was connected up to a gas burette filled with $H_2$ at approx. 1 atmosphere pressure. By means of a shaking machine the reaction vessel was shaken and the reaction started and maintained. Via measuring the $H_2$-take-up the reaction speed (turnover numbers) was determined for 1 hour. The results are given in tables E and F.

TABLE E

Hydrogenation of aromatic substrates with the aid of Rh-catalysts (0.5 weight % Rh on support).

| A | B | C | D | E | F | G | H | I |
|---|---|---|---|---|---|---|---|---|
| aniline.HCl | $Rh_4(CO)_{12}$ | $SrTiO_3$[b] | EtOH | 4.2 | 50 | 74 | — | — |
| benzophenone | $Rh_4(CO)_{12}$ | $TiO_2$-anatase[c] | MeOH | 1.3 | 25 | — | — | 32 |
| benzaldehyde | $Rh_4(CO)_{12}$ | $TiO_2$-anatase | MeOH | 6.7 | 31 | — | — | 150 |
| nitrobenzene | $Rh_4(CO)_{12}$ | $TiO_2$-anatase | MeOH | 6.7 | 24 | 265 | — | — |
| nitrobenzene | $Rh_4(CO)_{12}$ | $TiO_2$-anatase | MeOH/HCl | 6.7 | 24 | — | — | 370 |
| benzonitrile | $Rh_4(CO)_{12}$ | $TiO_2$-anatase | MeOH | 6.7 | 25 | — | — | 226 |
| benzonitrile | $Rh_4(CO)_{12}$ | $TiO_2$-anatase | MeOH/HCl | 6.7 | 25 | — | — | 71 |
| trans-stilbene | $Rh_4(CO)_{12}$ | $TiO_2$-anatase | MeOH | 0.4 | 20 | 0 | 4314[e] | — |
| trans-stilbene | $Rh_4(CO)_{12}$ | $TiO_2$-anatase | cyclohexane | 0.4 | 20 | 0 | 2876[ef] | — |
| cis-stilbene | $Rh_4(CO)_{12}$ | $TiO_2$-anatase | MeOH | 0.4 | 21 | 0 | 4709[e] | — |
| styrene | $Rh_4(CO)_{12}$ | $TiO_2$-anatase | MeOH | 0.4 | 22 | 612 | 15502[e] | — |
| phenylacetylene | $Rh_4(CO)_{12}$ | $TiO_2$-anatase | MeOH | 0.4 | 21 | 0 | 614 | — |
| phenylacetylene | $Rh_4(CO)_{12}$ | $TiO_2$-anatase | cyclohexane | 0.4 | 21 | 0 | 410 | — |
| diphenylacetylene | $Rh_4(CO)_{12}$ | $TiO_2$-anatase | MeOH | 0.4 | 21 | 0 | 4300[e] | — |
| phenol | $Rh_4(CO)_{12}$ | $TiO_2$-anatase | MeOH | 6.3 | 29 | 1314 | — | — |
| phenol | $Rh_4(CO)_{12}$ | $TiO_2$-anatase | $H_2O$ | 6.3[d] | 29 | 835 | — | — |
| phenol | $Rh_4(CO)_{12}$ | $SrTiO_3$ | EtOH | 6.3 | 30 | 1123 | — | — |
| phenol | $Rh_6(CO)_{16}$ | $SrTiO_3$ | EtOH | 6.3 | 30 | 619 | — | — |

A: Compound
B: Source Rh
C: Support
D: Solvent
E: Concentration mMol/ml
F: Temperature °C.
G: TN aromate function[a]
H: TN other function[a]
I: TN total[a]
[a]TN = turnover number = mAt H/mAt Rh/hour
[b]Ventron
[c]Bayer Titan A
[d]not everything was dissolved
[e]calculated values: as a result of fast reaction conversion time is <1 hour
[f]$^1$H—NMR: only product is 1,2-diphenylethane

TABLE F

Hydrogenation of non-aromatic substrates according to the method of example 8 with the aid of Rh-catalysts (0.5 weight % Rh[h] on support).

| Compound | Support | Solvent | Concentration mMol/ml | Temp. °C. | TN |
|---|---|---|---|---|---|
| acetone | $TiO_2$-anatase[a] | MeOH | 5 | 23 | 173 |
| cyclohexanone | $TiO_2$-anatase | MeOH | 6.3 | 30 | 0 |
| fructose | $TiO_2$-anatase | MeOH | 1 | 24 | 63 |
| fructose | $TiO_2$-anatase | $H_2O$ | 2.5 | 24 | 47 |
| nitromethane | $TiO_2$-anatase | MeOH | 5 | 27 | 0 |
| nitromethane | $TiO_2$-anatase | MeOH/HCl | 5 | 27 | 92[d] |
| acetonitrile | $TiO_2$-anatase | MeOH | 5 | 25 | 1007 |
| acetonitrile | $TiO_2$-anatase | MeOH/HCl | 5 | 25 | 148 |
| 2-methyl-1-pentene | $TiO_2$anatase | MeOH | 0.8 | 22 | 24783[f] |
| cyclohexene | $TiO_2$-anatase | cyclohexane | 0.8 | 20 | 19720[f] |
| cyclohexene | $TiO_2$anatase | MeOH | 0.8 | 20 | 28313[f] |
| cyclohexene | $SrTiO_3$[g] | cyclohexane | 0.4 | 22 | 17967[f] |
| α-pinene | $SrTiO_3$[g] | MeOH | 0.8 | 20 | 7292[f] |
| 1-octene | $TiO_2$-anatase[a] | MeOH | 0.8 | 21 | 31939[f] |
| 2-octene (cis) | $TiO_2$-anatase | MeOH | 0.8 | 22 | 19990[f] |
| 2-octene (cis) | $TiO_2$-anatase | cyclohexane | 0.8 | 22 | 5303[f] |
| geraniol | $TiO_2$-anatase | MeOH | 0.4 | 22 | 2448 |
| 1-pentyne | $TiO_2$-anatase | MeOH | 0.8 | 22 | 612 |
| 1-hexyne | $TiO_2$-anatase | MeOH | 0.8 | 19 | e[f] |

[a]Bayer Titan A
[b]TN = Turnover Number = mAt H/mAt Rh/hour
[c]GLC: product is 2-propanol
[d]$^1$H—NMR: $CH_3NH_3$.Cl present + some intermediate products
[e]1237 (2nd min) → 19580 (21st min)
[f]calculated values: as a result of fast reaction conversion time <1 hour
[g]Ventron
[h]Rh from $Rh_4(CO)_{12}$.

EXAMPLE 9

Hydrogenations of substrate in a solvent.

25 to 150 ml of solvent (ethanol, water), 35 to 200 mMol of substrate and 1.0 g of catalyst were placed in a double-walled hydrogenation vessel. The desired temperature was adjusted, the air above was replaced by $H_2$ and the vessel was connected up to a gas burette filled with $H_2$ at approx. 1 atmosphere pressure. The reaction was started and maintained by means of stirring; via measurement of the $H_2$ take-up the reaction speed (turnover numbers) was determined during several hours. Table G shows the results which were obtained with the above method.

TABLE G

Hydrogenation of aromatic substrates according to the method of example 9 with the aid of an Rh-catalyst (0.5 weight % Rh[d] on $TiO_2$-anatase)[e].

| Compound | solvent | Concentration mMol/ml | Temp. °C. | TN 1st hr[a]. | TN (after x hours)[a] |
|---|---|---|---|---|---|
| benzoic acid | EtOH | 8.2 | 63 | 202 | 162(4) |
| terephthalic acid | $H_2O$ | 0.3[b] | 67 | 70 | 43(8)[c] |
| di-Na-terephthalate | $H_2O$ | 0.7 | 60 | 38 | 24(3) |

[a]TN = Turnover Number = mAt H/mAt Rh/hour
[b]not everything was dissolved
[c]H-NMR: 1,4-cyclohexanedicarboxylic acid present
[d]Rh from $Rh_4(CO)_{12}$
[e]Bayer Titan A

EXAMPLE 10

Hydrogenations of substrate in the gas phase.

1 g of catalyst was placed in a cylindrical tube (1 cm diameter) between two cotton wads. Gas mixtures containing hydrogen and benzene were passed over the catalyst (at room temperature) and then through a cold drop (−80° C.). The condensate was analyzed after 0.5 hours and after 1.5 hours for the presence of cyclohexane and benzene ('H-NMR). Some results are shown in table H.

TABLE H

Hydrogenation of benzene in the gas phase; method according to example 10; catalyst 0.5 weight % Rh[a] on $TiO_2$-anatase[b].

| Compos. gas mixtures (%) | | | Total gas speed in ml/min | Mol relation Prods. in % | | |
|---|---|---|---|---|---|---|
| Benzene | Hydrogen | Methane | | $C_6H_6/H_2$ | cyclohexane | benzene |
| 5.8 | 94.2 | — | 63.7 | 1/16.2 | 100 | 0 |
| 2.5 | 6.8 | 90.7 | 50 | 1/2.7 | 50 | 50 |
| 2.5 | 10.0 | 87.5 | 50 | 1/4.0 | 53 | 47 |
| 2.5 | 11.8 | 85.7 | 50 | 1/4.7 | 92 | 8 |
| 2.5 | 13.5 | 84 | 50 | 1/5.4 | 100 | 0 |
| 0.1–0.5 | ≦5 | 94.9–94.5 | 50 | 1/50–1/10 | 100 | 0 |

[a]Rh from $Rh_4(CO)_{12}$
[b]Degussa P25

We claim:

1. Method for the preparation of catalysts on support materials which serve for the hydrogenation of unsaturated organic compounds, which catalysts consist of rhodium metal on support, obtained by applying rhodium carbonyl clusters to a support in an inert atmosphere of $N_2$ and then pyrolyzing them at a relatively low temperature of Tmax. 300° C., characterized in that the material which is thus applied to the support is activated by means of reaction with oxygen.

2. Method according to claim 1, characterized in that the pyrolyzing process takes place at temperatures between 100° C. and 300° C.

3. Method according to claim 1, characterized in that the activation of the catalyst by means of reaction with oxygen takes place at temperatures between 0° C. and 150° C.

4. Method according to claim 1, characterized in that the quantity of rhodium metal on support amounts to 0.5–2.5 weight percent of the total weight.

5. Method for the preparation of a catalyst according to claim 1, characerized in that the support material is strontium titanate.

6. Method according to claim 2, characterized in that the pyrolyzing process takes place at temperatures around 150° C.

* * * * *

UNITED STATES PATENT AND TRADEMARK OFFICE
CERTIFICATE OF CORRECTION

PATENT NO. : 4,831,008

DATED : May 16, 1989

INVENTOR(S) : Timmer et al.

It is certified that error appears in the above-identified patent and that said Letters Patent is hereby corrected as shown below:

Column 2, line 6, change "prefer" to --preferred--.

Column 4, line 29, omit "b".

Column 10, lines 28-29, delete excess space after "to the" and before "support";

Column 10, line 42, change "characerized" to --characterized--.

Signed and Sealed this

Thirteenth Day of October, 1992

*Attest:*

DOUGLAS B. COMER

*Attesting Officer*   Acting Commissioner of Patents and Trademarks